(12) United States Patent
Orts et al.

(10) Patent No.: US 11,779,316 B2
(45) Date of Patent: *Oct. 10, 2023

(54) BIOPSY DEVICE

(71) Applicant: Bard Peripheral Vascular, Inc., Franklin Lakes, NJ (US)

(72) Inventors: Soren Falkesgaard Orts, Virum (DK); Frederik Sonnenborg, Jyllinge (DK); Per Rosenberg Jensen, Holmegaard (DK); Brian Kim Larsen, Gislinge (DK)

(73) Assignee: Bard Peripheral Vascular, Inc., Franklin Lakes, NJ (US)

( * ) Notice: Subject to any disclaimer, the term of this patent is extended or adjusted under 35 U.S.C. 154(b) by 909 days.

This patent is subject to a terminal disclaimer.

(21) Appl. No.: 16/354,637

(22) Filed: Mar. 15, 2019

(65) Prior Publication Data

US 2019/0209144 A1 Jul. 11, 2019

Related U.S. Application Data

(63) Continuation of application No. 14/772,994, filed as application No. PCT/US2014/031224 on Mar. 19, 2014, now Pat. No. 10,285,673.

(Continued)

(51) Int. Cl.
*A61B 10/02* (2006.01)
*A61B 10/00* (2006.01)
*A61B 17/29* (2006.01)

(52) U.S. Cl.
CPC ...... *A61B 10/0275* (2013.01); *A61B 10/0096* (2013.01); *A61B 10/0283* (2013.01);
(Continued)

(58) Field of Classification Search
CPC ............ A61B 10/0275; A61B 10/0096; A61B 10/0283; A61B 2010/0208; A61B 2017/2923
See application file for complete search history.

(56) References Cited

U.S. PATENT DOCUMENTS 737,293 A 8/1903 Summerfeldt
1,087,845 A * 2/1914 Stevens .............. A61M 25/0113
604/159

(Continued)

FOREIGN PATENT DOCUMENTS

CN 101011268 A 8/2007
CN 101032420 A 9/2007
(Continued)

OTHER PUBLICATIONS

Maxim; Maxim8606; USB/AC Adapter, Li+ Linear Battery Charger with Integrated 50m Omega Battery Switch in TDFN; http://datasheets.maxim-ic.com/en/ds/MAX8606.pdf; Dec. 2008; pp. 1-14; Rev 1.

*Primary Examiner* — Rene T Towa
(74) *Attorney, Agent, or Firm* — Dinsmore & Shohl LLP

(57) ABSTRACT

A biopsy device includes a cutting cannula and an inner member. The inner member has a rotatable toothed rack, a sharpened distal tip, and a sample notch. The inner member is configured to be received in the cutting cannula. The rotatable toothed rack has a proximal portion and a rotation zone in the proximal portion. The rotation zone of the rotatable toothed rack has circumferential toothing configured as a series of longitudinally spaced cut-outs that run around an entire circumference of the rotatable toothed rack to facilitate both a longitudinal movement and a rotational movement of the rotatable toothed rack and inner member. A drive is configured to engage the circumferential toothing (Continued)

to move the rotatable toothed rack within the cutting cannula in at least one of the longitudinal movement and the rotational movement.

19 Claims, 5 Drawing Sheets

Related U.S. Application Data

(60) Provisional application No. 61/803,626, filed on Mar. 20, 2013.

(52) U.S. Cl.
CPC ............. *A61B 2010/0208* (2013.01); *A61B 2017/2923* (2013.01)

(56) References Cited

U.S. PATENT DOCUMENTS

| | | |
|---|---|---|
| 1,585,934 A | 5/1926 | Muir |
| 1,663,761 A | 3/1928 | Johnson |
| 2,953,934 A | 9/1960 | Sundt |
| 3,019,733 A | 2/1962 | Braid |
| 3,224,434 A | 12/1965 | Molomut et al. |
| 3,289,669 A | 12/1966 | Dwyer et al. |
| 3,477,423 A | 11/1969 | Griffith |
| 3,512,519 A | 5/1970 | Hall |
| 3,561,429 A | 2/1971 | Jewett et al. |
| 3,565,074 A | 2/1971 | Foti |
| 3,606,878 A | 9/1971 | Kellogg |
| 3,727,602 A | 4/1973 | Hyden et al. |
| 3,732,858 A | 5/1973 | Banko |
| 3,785,380 A | 1/1974 | Brumfield |
| 3,800,783 A | 4/1974 | Jamshidi |
| 3,844,272 A | 10/1974 | Banko |
| 3,882,849 A | 5/1975 | Jamshidi |
| 3,889,682 A | 6/1975 | Denis et al. |
| 3,916,948 A | 11/1975 | Benjamin |
| 4,275,730 A | 6/1981 | Hussein |
| 4,282,884 A | 8/1981 | Boebel |
| 4,306,570 A | 12/1981 | Matthews |
| 4,354,092 A | 10/1982 | Manabe et al. |
| 4,393,879 A | 7/1983 | Milgrom |
| 4,445,509 A | 5/1984 | Auth |
| 4,490,137 A | 12/1984 | Moukheibir |
| 4,549,554 A | 10/1985 | Markham |
| 4,577,629 A | 3/1986 | Martinez |
| 4,589,414 A | 5/1986 | Yoshida et al. |
| 4,603,694 A | 8/1986 | Wheeler |
| 4,605,011 A | 8/1986 | Naslund |
| 4,616,215 A | 10/1986 | Maddalena |
| 4,617,430 A | 10/1986 | Bryant |
| 4,620,539 A | 11/1986 | Andrews et al. |
| 4,643,197 A | 2/1987 | Greene et al. |
| 4,645,153 A | 2/1987 | Granzow et al. |
| 4,678,459 A | 7/1987 | Onik et al. |
| 4,696,298 A | 9/1987 | Higgins et al. |
| 4,702,260 A | 10/1987 | Wang |
| 4,706,687 A | 11/1987 | Rogers |
| 4,735,215 A * | 4/1988 | Goto ................ A61B 10/0275 600/567 |
| 4,776,346 A | 10/1988 | Beraha et al. |
| 4,792,327 A | 12/1988 | Swartz |
| 4,832,044 A | 5/1989 | Garg |
| 4,844,064 A | 7/1989 | Thimsen et al. |
| 4,844,087 A | 7/1989 | Garg |
| 4,850,354 A | 7/1989 | McGurk-Burleson et al. |
| 4,893,635 A | 1/1990 | de Groot et al. |
| 4,907,598 A | 3/1990 | Bauer |
| RE33,258 E | 7/1990 | Onik et al. |
| 4,940,061 A | 7/1990 | Terwilliger et al. |
| 4,952,817 A | 8/1990 | Bolan et al. |
| 4,958,625 A | 9/1990 | Bates et al. |
| 4,967,762 A | 11/1990 | DeVries |
| 4,986,278 A | 1/1991 | Ravid et al. |
| 4,986,279 A | 1/1991 | O'Neill |
| 4,986,807 A | 1/1991 | Farr |
| 4,989,614 A | 2/1991 | Dejter, Jr. et al. |
| 5,025,797 A | 6/1991 | Baran |
| 5,048,538 A | 9/1991 | Terwilliger et al. |
| 5,057,822 A | 10/1991 | Hoffman |
| 5,078,603 A | 1/1992 | Cohen |
| 5,125,413 A | 6/1992 | Baran |
| 5,138,245 A | 8/1992 | Mattinger et al. |
| 5,146,921 A | 9/1992 | Terwilliger et al. |
| 5,156,160 A | 10/1992 | Bennett |
| 5,158,528 A | 10/1992 | Walker et al. |
| 5,172,702 A | 12/1992 | Leigh et al. |
| 5,176,628 A | 1/1993 | Charles et al. |
| 5,180,352 A | 2/1993 | Terwilliger |
| 5,197,484 A | 3/1993 | Kornberg et al. |
| 5,211,627 A | 5/1993 | William |
| 5,223,012 A | 6/1993 | Best et al. |
| 5,225,763 A | 7/1993 | Krohn et al. |
| 5,234,000 A | 8/1993 | Hakky et al. |
| 5,236,334 A | 8/1993 | Bennett |
| 5,242,404 A | 9/1993 | Conley et al. |
| 5,249,583 A | 10/1993 | Mallaby |
| 5,254,117 A | 10/1993 | Rigby et al. |
| 5,282,476 A | 2/1994 | Terwilliger |
| 5,282,477 A | 2/1994 | Bauer |
| 5,290,253 A | 3/1994 | Kira |
| 5,305,762 A | 4/1994 | Acorn et al. |
| 5,324,306 A | 6/1994 | Makower et al. |
| 5,334,183 A | 8/1994 | Wuchinich |
| 5,335,671 A | 8/1994 | Clement |
| 5,368,029 A | 11/1994 | Holcombe et al. |
| 5,368,045 A | 11/1994 | Clement et al. |
| 5,383,874 A | 1/1995 | Jackson et al. |
| 5,397,462 A | 3/1995 | Higashijima et al. |
| 5,400,798 A | 3/1995 | Baran |
| 5,439,474 A | 8/1995 | Li |
| 5,458,112 A | 10/1995 | Weaver |
| 5,469,860 A | 11/1995 | De Santis |
| 5,471,994 A | 12/1995 | Guirguis |
| 5,479,486 A | 12/1995 | Saji |
| 5,485,917 A | 1/1996 | Early |
| 5,492,130 A | 2/1996 | Chiou |
| 5,511,556 A | 4/1996 | DeSantis |
| 5,526,822 A | 6/1996 | Burbank et al. |
| 5,535,755 A | 7/1996 | Heske |
| 5,546,957 A | 8/1996 | Heske |
| 5,554,151 A | 9/1996 | Hinchliffe |
| 5,560,373 A | 10/1996 | De Santis |
| 5,564,436 A | 10/1996 | Hakky et al. |
| 5,569,284 A | 10/1996 | Young et al. |
| 5,575,293 A | 11/1996 | Miller et al. |
| 5,591,170 A | 1/1997 | Spievack et al. |
| 5,601,583 A | 2/1997 | Donahue et al. |
| 5,601,585 A | 2/1997 | Banik et al. |
| 5,602,449 A | 2/1997 | Krause et al. |
| 5,612,738 A | 3/1997 | Kim |
| 5,617,874 A | 4/1997 | Baran |
| 5,649,547 A | 7/1997 | Ritchart et al. |
| 5,655,542 A | 8/1997 | Weilandt |
| 5,655,657 A | 8/1997 | Roshdy |
| 5,665,101 A | 9/1997 | Becker et al. |
| 5,669,394 A | 9/1997 | Bergey et al. |
| 5,699,909 A | 12/1997 | Foster |
| 5,700,265 A | 12/1997 | Romano |
| 5,709,697 A | 1/1998 | Ratcliff et al. |
| 5,720,760 A | 2/1998 | Becker et al. |
| 5,735,264 A | 4/1998 | Siczek et al. |
| 5,752,923 A | 5/1998 | Terwilliger |
| 5,755,714 A | 5/1998 | Murphy-Chutorian |
| 5,766,135 A | 6/1998 | Terwilliger |
| 5,769,086 A | 6/1998 | Ritchart et al. |
| 5,769,795 A | 6/1998 | Terwilliger |
| 5,775,333 A | 7/1998 | Burbank et al. |
| 5,779,649 A | 7/1998 | Herbert |
| 5,788,651 A | 8/1998 | Weilandt |
| 5,792,167 A | 8/1998 | Kablik et al. |
| 5,807,282 A | 9/1998 | Fowler |

(56) References Cited

U.S. PATENT DOCUMENTS

| | | | |
|---|---|---|---|
| 5,817,033 A | 10/1998 | DeSantis et al. |
| 5,817,034 A | 10/1998 | Milliman et al. |
| 5,823,970 A | 10/1998 | Terwilliger |
| 5,827,305 A | 10/1998 | Gordon |
| 5,830,219 A | 11/1998 | Bird et al. |
| D403,405 S | 12/1998 | Terwilliger |
| 5,857,982 A | 1/1999 | Milliman et al. |
| 5,871,699 A | 2/1999 | Ruggeri |
| 5,879,365 A | 3/1999 | Whitfield et al. |
| 5,908,233 A | 6/1999 | Heskett et al. |
| 5,913,857 A | 6/1999 | Ritchart et al. |
| 5,916,198 A | 6/1999 | Dillow |
| 5,916,229 A | 6/1999 | Evans |
| 5,928,164 A | 7/1999 | Burbank et al. |
| 5,944,673 A | 8/1999 | Gregoire et al. |
| 5,951,490 A | 9/1999 | Fowler |
| 5,951,575 A | 9/1999 | Bolduc et al. |
| 5,964,716 A | 10/1999 | Gregoire et al. |
| 5,971,939 A | 10/1999 | DeSantis et al. |
| 5,976,164 A | 11/1999 | Bencini et al. |
| 5,980,469 A | 11/1999 | Burbank et al. |
| 5,980,545 A | 11/1999 | Pacala et al. |
| 6,007,495 A | 12/1999 | Matula |
| 6,007,497 A | 12/1999 | Huitema |
| 6,007,556 A | 12/1999 | Kablik et al. |
| 6,017,316 A | 1/2000 | Ritchart et al. |
| 6,018,227 A | 1/2000 | Kumar et al. |
| 6,019,733 A | 2/2000 | Farascioni |
| 6,022,324 A | 2/2000 | Skinner |
| 6,022,325 A | 2/2000 | Siczek et al. |
| 6,027,458 A | 2/2000 | Janssens |
| 6,032,673 A | 3/2000 | Savage et al. |
| 6,036,657 A | 3/2000 | Milliman et al. |
| 6,050,955 A | 4/2000 | Bryan et al. |
| 6,055,870 A | 5/2000 | Jaeger |
| 6,071,247 A | 6/2000 | Kennedy |
| 6,077,230 A | 6/2000 | Gregoire et al. |
| 6,083,176 A | 7/2000 | Terwilliger |
| 6,083,237 A | 7/2000 | Huitema et al. |
| 6,086,544 A | 7/2000 | Hibner et al. |
| 6,106,484 A | 8/2000 | Terwilliger |
| 6,110,129 A | 8/2000 | Terwilliger |
| 6,120,462 A | 9/2000 | Hibner et al. |
| 6,123,957 A | 9/2000 | Jernberg |
| 6,126,617 A | 10/2000 | Weilandt et al. |
| 6,142,955 A | 11/2000 | Farascioni et al. |
| 6,162,187 A | 12/2000 | Buzzard et al. |
| 6,165,136 A | 12/2000 | Nishtala |
| 6,193,673 B1 | 2/2001 | Viola et al. |
| 6,196,978 B1 | 3/2001 | Weilandt et al. |
| 6,213,957 B1 | 4/2001 | Milliman et al. |
| 6,220,248 B1 | 4/2001 | Voegele et al. |
| 6,231,522 B1 | 5/2001 | Voegele et al. |
| 6,241,687 B1 | 6/2001 | Voegele et al. |
| 6,267,759 B1 | 7/2001 | Quick |
| 6,273,861 B1 | 8/2001 | Bates et al. |
| 6,273,862 B1 | 8/2001 | Privitera et al. |
| 6,280,398 B1 | 8/2001 | Ritchart et al. |
| 6,283,925 B1 | 9/2001 | Terwilliger |
| 6,322,523 B2 | 11/2001 | Weilandt et al. |
| 6,328,701 B1 | 12/2001 | Terwilliger |
| 6,331,166 B1 | 12/2001 | Burbank et al. |
| 6,358,217 B1 | 3/2002 | Bourassa |
| 6,361,504 B1* | 3/2002 | Shin ............. A61B 10/0233 |
| | | | 600/562 |
| 6,402,701 B1 | 6/2002 | Kaplan et al. |
| 6,419,641 B1 | 7/2002 | Mark et al. |
| 6,428,486 B2 | 8/2002 | Ritchart et al. |
| 6,428,487 B1 | 8/2002 | Burdorff et al. |
| 6,432,064 B1 | 8/2002 | Hibner et al. |
| 6,432,065 B1 | 8/2002 | Burdorff et al. |
| 6,434,507 B1 | 8/2002 | Clayton et al. |
| 6,436,054 B1 | 8/2002 | Viola et al. |
| 6,461,302 B1 | 10/2002 | Thompson |
| 6,471,659 B2 | 10/2002 | Eggers et al. |
| 6,482,158 B2 | 11/2002 | Mault |
| 6,485,436 B1 | 11/2002 | Truckai et al. |
| 6,488,636 B2 | 12/2002 | Bryan et al. |
| 6,494,844 B1 | 12/2002 | Van Bladel et al. |
| 6,527,736 B1 | 3/2003 | Attinger et al. |
| 6,540,694 B1 | 4/2003 | Van Bladel et al. |
| 6,540,761 B2 | 4/2003 | Houser |
| 6,544,194 B1 | 4/2003 | Kortenbach et al. |
| 6,551,255 B2 | 4/2003 | Van Bladel et al. |
| 6,554,779 B2 | 4/2003 | Viola et al. |
| 6,585,664 B2 | 7/2003 | Burdorff et al. |
| 6,585,694 B1* | 7/2003 | Smith ............. A61M 25/0084 |
| | | | 604/164.12 |
| 6,586,585 B1 | 7/2003 | Bastian |
| 6,592,530 B1 | 7/2003 | Farhadi |
| 6,626,849 B2 | 9/2003 | Huitema et al. |
| 6,632,182 B1 | 10/2003 | Treat |
| 6,638,235 B2 | 10/2003 | Miller et al. |
| 6,656,133 B2 | 12/2003 | Voegele et al. |
| 6,659,105 B2 | 12/2003 | Burbank et al. |
| 6,659,338 B2 | 12/2003 | Dittmann et al. |
| 6,683,439 B2 | 1/2004 | Takano et al. |
| 6,689,072 B2 | 2/2004 | Kaplan et al. |
| 6,695,786 B2 | 2/2004 | Wang et al. |
| 6,702,832 B2 | 3/2004 | Ross et al. |
| 6,712,773 B1 | 3/2004 | Viola |
| 6,712,774 B2 | 3/2004 | Voegele et al. |
| 6,752,768 B2 | 6/2004 | Burdorff et al. |
| 6,753,671 B1 | 6/2004 | Harvey |
| 6,755,802 B2 | 6/2004 | Bell |
| 6,758,824 B1 | 7/2004 | Miller et al. |
| 6,764,495 B2 | 7/2004 | Lee et al. |
| 6,832,990 B2 | 12/2004 | Kortenbach et al. |
| 6,849,080 B2 | 2/2005 | Lee et al. |
| 6,850,159 B1 | 2/2005 | Mudge |
| 6,860,860 B2 | 3/2005 | Viola |
| 6,875,183 B2 | 4/2005 | Cervi |
| 6,887,210 B2 | 5/2005 | Quay |
| 6,908,440 B2 | 6/2005 | Fisher |
| D508,458 S | 8/2005 | Solland et al. |
| 6,926,676 B2 | 8/2005 | Turturro et al. |
| 6,984,213 B2 | 1/2006 | Horner et al. |
| 7,004,174 B2 | 2/2006 | Eggers et al. |
| 7,010,332 B1 | 3/2006 | Irvin et al. |
| 7,025,732 B2 | 4/2006 | Thompson et al. |
| D525,583 S | 7/2006 | Vu |
| 7,108,660 B2 | 9/2006 | Stephens et al. |
| 7,153,274 B2 | 12/2006 | Stephens et al. |
| 7,156,814 B1 | 1/2007 | Williamson, IV et al. |
| 7,182,754 B2 | 2/2007 | Brigham et al. |
| 7,189,206 B2 | 3/2007 | Quick et al. |
| 7,189,207 B2 | 3/2007 | Viola |
| 7,219,867 B2 | 5/2007 | Kalis et al. |
| 7,226,424 B2 | 6/2007 | Ritchart et al. |
| 7,252,641 B2 | 8/2007 | Thompson et al. |
| 7,276,032 B2 | 10/2007 | Hibner |
| 7,328,794 B2 | 2/2008 | Lubs et al. |
| 7,347,828 B2 | 3/2008 | Francese et al. |
| 7,347,829 B2 | 3/2008 | Mark et al. |
| 7,374,544 B2 | 5/2008 | Freeman et al. |
| 7,390,306 B2 | 6/2008 | Mark |
| 7,397,654 B2 | 7/2008 | Mori |
| 7,402,140 B2 | 7/2008 | Spero et al. |
| 7,405,536 B2 | 7/2008 | Watts |
| 7,407,054 B2 | 8/2008 | Seiler et al. |
| 7,419,472 B2 | 9/2008 | Hibner et al. |
| 7,432,813 B2 | 10/2008 | Postma |
| 7,452,367 B2 | 11/2008 | Rassman et al. |
| 7,458,940 B2 | 12/2008 | Miller |
| 7,464,040 B2 | 12/2008 | Joao |
| 7,473,232 B2 | 1/2009 | Teague |
| 7,481,775 B2 | 1/2009 | Weikel, Jr. et al. |
| 7,490,048 B2 | 2/2009 | Joao |
| 7,491,177 B2 | 2/2009 | Hibner |
| 7,494,473 B2 | 2/2009 | Eggers et al. |
| 7,497,833 B2 | 3/2009 | Miller |
| 7,510,534 B2 | 3/2009 | Burdorff et al. |
| 7,513,877 B2 | 4/2009 | Viola |
| 7,517,321 B2 | 4/2009 | McCullough et al. |

(56) References Cited

U.S. PATENT DOCUMENTS

| | | |
|---|---|---|
| 7,517,322 B2 | 4/2009 | Weikel, Jr. et al. |
| 7,549,978 B2 | 6/2009 | Carlson et al. |
| 7,575,557 B2 | 8/2009 | Morton et al. |
| 7,648,466 B2 | 1/2010 | Stephens et al. |
| 7,670,299 B2 | 3/2010 | Beckman et al. |
| 7,717,861 B2 | 5/2010 | Weikel et al. |
| 7,727,164 B2 | 6/2010 | Cicenas et al. |
| 7,740,594 B2 | 6/2010 | Hibner |
| 7,740,596 B2 | 6/2010 | Hibner |
| 7,740,597 B2 | 6/2010 | Cicenas et al. |
| 7,758,515 B2 | 7/2010 | Hibner |
| 7,762,961 B2 | 7/2010 | Heske et al. |
| 7,806,834 B2 | 10/2010 | Beckman et al. |
| 7,828,746 B2 | 11/2010 | Teague |
| 7,828,747 B2 | 11/2010 | Heske et al. |
| 7,841,991 B2 | 11/2010 | Douglas et al. |
| 7,846,109 B2 | 12/2010 | Parihar et al. |
| 7,854,706 B2 | 12/2010 | Hibner |
| 7,862,517 B2 | 1/2011 | Tsonton et al. |
| 7,862,518 B2 | 1/2011 | Parihar |
| 7,871,384 B2 | 1/2011 | Thompson et al. |
| 7,883,476 B2 | 2/2011 | Miller et al. |
| 7,883,494 B2 | 2/2011 | Martin |
| 7,906,076 B2 | 3/2011 | Fischer |
| 7,914,462 B2 | 3/2011 | Hutchins et al. |
| 7,959,580 B2 | 6/2011 | Mccullough et al. |
| 7,974,681 B2 | 7/2011 | Wallace et al. |
| 8,002,713 B2 | 8/2011 | Heske et al. |
| 8,012,102 B2 | 9/2011 | McCullough et al. |
| 8,016,772 B2 | 9/2011 | Heske et al. |
| 8,016,844 B2 | 9/2011 | Privitera et al. |
| 8,052,614 B2 | 11/2011 | Heske et al. |
| 8,052,615 B2 | 11/2011 | Reuber et al. |
| 8,057,402 B2 | 11/2011 | Hibner et al. |
| 8,073,008 B2 | 12/2011 | Mehta et al. |
| 8,075,495 B2 | 12/2011 | Andreyko et al. |
| 8,083,671 B2 | 12/2011 | Boulais et al. |
| 8,083,687 B2 | 12/2011 | Parihar |
| 8,109,885 B2 | 2/2012 | Heske et al. |
| 8,118,755 B2 | 2/2012 | Hibner et al. |
| 8,152,738 B2 | 4/2012 | Li et al. |
| 8,157,744 B2 | 4/2012 | Jorgensen et al. |
| 8,162,851 B2 | 4/2012 | Heske et al. |
| 8,172,771 B2 | 5/2012 | Miller et al. |
| 8,172,773 B2 | 5/2012 | Heske et al. |
| 8,187,204 B2 | 5/2012 | Miller et al. |
| 8,190,238 B2 | 5/2012 | Moll et al. |
| 8,206,409 B2 | 6/2012 | Privitera et al. |
| 8,251,916 B2 | 8/2012 | Speeg et al. |
| 8,251,917 B2 | 8/2012 | Almazan |
| 8,262,585 B2 | 9/2012 | Thompson et al. |
| 8,262,586 B2 | 9/2012 | Anderson et al. |
| 8,267,868 B2 | 9/2012 | Taylor et al. |
| 8,277,393 B2 | 10/2012 | Miller et al. |
| 8,282,574 B2 | 10/2012 | Coonahan et al. |
| 8,283,890 B2 | 10/2012 | Videbaek |
| 8,287,465 B2 | 10/2012 | Hardin et al. |
| 8,313,444 B2 | 11/2012 | Thompson et al. |
| 8,343,069 B2 | 1/2013 | Uchiyama et al. |
| 8,366,636 B2 | 2/2013 | Videbaek |
| 8,430,824 B2 | 4/2013 | Videbaek et al. |
| 8,430,825 B2 | 4/2013 | Mark |
| 8,430,827 B2 | 4/2013 | Nicoson et al. |
| 8,485,987 B2 | 7/2013 | Videbaek et al. |
| 8,485,989 B2 | 7/2013 | Videbaek |
| 8,597,205 B2 | 12/2013 | Seiger et al. |
| 8,597,206 B2 | 12/2013 | Videbaek |
| 8,690,793 B2 | 4/2014 | Ranpura et al. |
| 8,702,621 B2 | 4/2014 | Mccullough et al. |
| 8,702,622 B2 | 4/2014 | McCullough et al. |
| 8,708,928 B2 | 4/2014 | Videbaek |
| 8,708,929 B2 | 4/2014 | Videbaek |
| 8,708,930 B2 | 4/2014 | Videbaek |
| 8,721,563 B2 | 5/2014 | Taylor et al. |
| 8,728,003 B2 | 5/2014 | Taylor et al. |
| 8,728,004 B2 | 5/2014 | Heske et al. |
| 8,771,200 B2 * | 7/2014 | Thompson ......... A61B 10/0283 600/568 |
| 8,808,197 B2 | 8/2014 | Videbaek |
| 8,858,463 B2 | 10/2014 | Seiger et al. |
| 8,864,680 B2 | 10/2014 | Videbaek et al. |
| 8,926,527 B2 | 1/2015 | Jørgensen et al. |
| 8,951,208 B2 | 2/2015 | Almazan |
| 8,951,209 B2 | 2/2015 | Heske et al. |
| 8,956,306 B2 | 2/2015 | Hibner |
| 8,961,430 B2 | 2/2015 | Coonahan et al. |
| 8,992,440 B2 | 3/2015 | Reuber et al. |
| 9,072,502 B2 | 7/2015 | Heske et al. |
| 9,161,743 B2 | 10/2015 | Mccullough et al. |
| 9,173,641 B2 | 11/2015 | Chudzik et al. |
| 9,282,949 B2 | 3/2016 | Videbaek |
| 9,345,458 B2 | 5/2016 | Videbaek et al. |
| 9,421,002 B2 | 8/2016 | Heske et al. |
| 9,439,631 B2 | 9/2016 | Heske et al. |
| 9,439,632 B2 | 9/2016 | Almazan |
| 9,456,809 B2 | 10/2016 | Jorgensen et al. |
| 10,058,308 B2 | 8/2018 | Mccullough et al. |
| 10,149,664 B2 | 12/2018 | Anderson et al. |
| 2001/0007925 A1 | 7/2001 | Ritchart et al. |
| 2001/0011156 A1 | 8/2001 | Viola et al. |
| 2001/0012919 A1 | 8/2001 | Terwilliger |
| 2001/0014779 A1 | 8/2001 | Burbank et al. |
| 2001/0034530 A1 | 10/2001 | Malackowski et al. |
| 2001/0044595 A1 | 11/2001 | Reydel et al. |
| 2001/0047183 A1 | 11/2001 | Privitera et al. |
| 2002/0000403 A1 | 1/2002 | Tanaka et al. |
| 2002/0029007 A1 | 3/2002 | Bryan et al. |
| 2002/0055689 A1 * | 5/2002 | Kaplan ............. A61B 10/0233 600/567 |
| 2002/0067151 A1 | 6/2002 | Tanishita |
| 2002/0068878 A1 | 6/2002 | Jasonni et al. |
| 2002/0082518 A1 | 6/2002 | Weiss et al. |
| 2002/0107043 A1 | 8/2002 | Adamson et al. |
| 2002/0115942 A1 | 8/2002 | Stanford et al. |
| 2002/0120212 A1 | 8/2002 | Ritchart et al. |
| 2002/0143269 A1 | 10/2002 | Neuenfeldt |
| 2002/0156395 A1 | 10/2002 | Stephens et al. |
| 2003/0023188 A1 | 1/2003 | Kritzman et al. |
| 2003/0023239 A1 | 1/2003 | Burbank et al. |
| 2003/0073929 A1 | 4/2003 | Baltschun et al. |
| 2003/0093103 A1 | 5/2003 | Malackowski et al. |
| 2003/0130593 A1 | 7/2003 | Gonzalez |
| 2003/0130677 A1 | 7/2003 | Whitman et al. |
| 2003/0163142 A1 | 8/2003 | Paltieli et al. |
| 2003/0229293 A1 | 12/2003 | Hibner et al. |
| 2003/0233101 A1 | 12/2003 | Lubock et al. |
| 2004/0015079 A1 | 1/2004 | Berger et al. |
| 2004/0019297 A1 | 1/2004 | Angel |
| 2004/0030367 A1 | 2/2004 | Yamaki et al. |
| 2004/0034280 A1 | 2/2004 | Privitera et al. |
| 2004/0049128 A1 | 3/2004 | Miller et al. |
| 2004/0054299 A1 | 3/2004 | Burdorff et al. |
| 2004/0082915 A1 | 4/2004 | Kadan |
| 2004/0092980 A1 | 5/2004 | Cesarini et al. |
| 2004/0092992 A1 | 5/2004 | Adams et al. |
| 2004/0162505 A1 | 8/2004 | Kaplan et al. |
| 2004/0167428 A1 | 8/2004 | Quick et al. |
| 2004/0186393 A1 | 9/2004 | Leigh et al. |
| 2004/0210161 A1 | 10/2004 | Burdorff et al. |
| 2004/0215103 A1 | 10/2004 | Mueller, Jr. et al. |
| 2004/0220495 A1 | 11/2004 | Cahir et al. |
| 2004/0230135 A1 | 11/2004 | Merkle |
| 2004/0230188 A1 | 11/2004 | Cioanta et al. |
| 2004/0249278 A1 | 12/2004 | Krause |
| 2004/0267157 A1 | 12/2004 | Miller et al. |
| 2005/0004492 A1 | 1/2005 | Burbank et al. |
| 2005/0004559 A1 | 1/2005 | Quick et al. |
| 2005/0010131 A1 | 1/2005 | Burbank et al. |
| 2005/0020909 A1 | 1/2005 | Moctezuma de la Barrera et al. |
| 2005/0027210 A1 | 2/2005 | Miller |
| 2005/0049489 A1 | 3/2005 | Foerster et al. |
| 2005/0049521 A1 | 3/2005 | Miller et al. |
| 2005/0054947 A1 | 3/2005 | Goldenberg |
| 2005/0065453 A1 | 3/2005 | Shabaz et al. |

(56) References Cited

U.S. PATENT DOCUMENTS

| | | |
|---|---|---|
| 2005/0085838 A1 | 4/2005 | Thompson et al. |
| 2005/0088120 A1 | 4/2005 | Avis |
| 2005/0101879 A1 | 5/2005 | Shidham et al. |
| 2005/0113715 A1 | 5/2005 | Schwindt et al. |
| 2005/0113716 A1 | 5/2005 | Mueller, Jr. et al. |
| 2005/0124914 A1* | 6/2005 | Dicarlo .............. A61B 10/0275 600/567 |
| 2005/0124915 A1 | 6/2005 | Eggers et al. |
| 2005/0177117 A1 | 8/2005 | Crocker et al. |
| 2005/0193451 A1 | 9/2005 | Quistgaard et al. |
| 2005/0209530 A1 | 9/2005 | Pflueger |
| 2005/0215921 A1 | 9/2005 | Hibner et al. |
| 2005/0275378 A1 | 12/2005 | Canino et al. |
| 2005/0277829 A1 | 12/2005 | Tsonton et al. |
| 2005/0277871 A1 | 12/2005 | Seiis |
| 2005/0288605 A1 | 12/2005 | Pellegrino et al. |
| 2006/0030784 A1 | 2/2006 | Miller et al. |
| 2006/0074344 A1 | 4/2006 | Hibner |
| 2006/0074345 A1 | 4/2006 | Hibner |
| 2006/0074350 A1 | 4/2006 | Cash |
| 2006/0113958 A1 | 6/2006 | Lobert et al. |
| 2006/0116603 A1 | 6/2006 | Shibazaki et al. |
| 2006/0122535 A1 | 6/2006 | Daum |
| 2006/0129063 A1 | 6/2006 | Thompson et al. |
| 2006/0149162 A1 | 7/2006 | Daw et al. |
| 2006/0173377 A1* | 8/2006 | McCullough ...... A61B 10/0275 600/566 |
| 2006/0178666 A1 | 8/2006 | Cosman et al. |
| 2006/0184063 A1 | 8/2006 | Miller |
| 2006/0241515 A1 | 10/2006 | Jones et al. |
| 2006/0258956 A1 | 11/2006 | Haberstich et al. |
| 2006/0260994 A1 | 11/2006 | Mark et al. |
| 2007/0016101 A1* | 1/2007 | Feldman ............ A61B 10/0275 600/567 |
| 2007/0032741 A1 | 2/2007 | Hibner et al. |
| 2007/0032743 A1 | 2/2007 | Hibner |
| 2007/0055173 A1 | 3/2007 | DeLonzor et al. |
| 2007/0073326 A1 | 3/2007 | Miller et al. |
| 2007/0090788 A1 | 4/2007 | Hansford et al. |
| 2007/0106176 A1 | 5/2007 | Mark et al. |
| 2007/0118048 A1 | 5/2007 | Stephens et al. |
| 2007/0118049 A1 | 5/2007 | Viola |
| 2007/0123797 A1 | 5/2007 | Krause |
| 2007/0161925 A1 | 7/2007 | Quick et al. |
| 2007/0167736 A1 | 7/2007 | Dietz et al. |
| 2007/0167782 A1 | 7/2007 | Callahan et al. |
| 2007/0167828 A1 | 7/2007 | Saadat |
| 2007/0167943 A1 | 7/2007 | Janssen et al. |
| 2007/0179401 A1 | 8/2007 | Hibner |
| 2007/0208271 A1* | 9/2007 | Voegele ............ A61B 10/0275 600/564 |
| 2007/0213590 A1 | 9/2007 | Squicciarini |
| 2007/0213630 A1 | 9/2007 | Beckman et al. |
| 2007/0213632 A1 | 9/2007 | Okazaki et al. |
| 2007/0219572 A1 | 9/2007 | Deck et al. |
| 2007/0236180 A1 | 10/2007 | Rodgers |
| 2007/0239067 A1 | 10/2007 | Hibner et al. |
| 2007/0255173 A1 | 11/2007 | Hibner |
| 2007/0270710 A1 | 11/2007 | Frass et al. |
| 2007/0276288 A1 | 11/2007 | Khaw |
| 2007/0287933 A1 | 12/2007 | Phan et al. |
| 2007/0292858 A1 | 12/2007 | Chen et al. |
| 2007/0293788 A1 | 12/2007 | Entrekin et al. |
| 2007/0293830 A1 | 12/2007 | Martin |
| 2008/0004545 A1 | 1/2008 | Garrison |
| 2008/0007217 A1 | 1/2008 | Riley |
| 2008/0021487 A1 | 1/2008 | Heisler |
| 2008/0021488 A1 | 1/2008 | Berberich |
| 2008/0030170 A1 | 2/2008 | Dacquay et al. |
| 2008/0064925 A1 | 3/2008 | Gill et al. |
| 2008/0064984 A1 | 3/2008 | Pflueger |
| 2008/0079391 A1 | 4/2008 | Schroeck et al. |
| 2008/0103411 A1 | 5/2008 | Van Bladel et al. |
| 2008/0110261 A1 | 5/2008 | Randall et al. |
| 2008/0125634 A1 | 5/2008 | Ryan et al. |
| 2008/0135443 A1 | 6/2008 | Frojd et al. |
| 2008/0146962 A1 | 6/2008 | Ritchie et al. |
| 2008/0146965 A1 | 6/2008 | Privitera et al. |
| 2008/0154151 A1 | 6/2008 | Ritchart et al. |
| 2008/0161682 A1 | 7/2008 | Kendrick et al. |
| 2008/0161718 A1 | 7/2008 | Schwindt |
| 2008/0161719 A1 | 7/2008 | Miller et al. |
| 2008/0161720 A1 | 7/2008 | Nicoson et al. |
| 2008/0195066 A1 | 8/2008 | Speeg et al. |
| 2008/0200833 A1 | 8/2008 | Hardin et al. |
| 2008/0200836 A1 | 8/2008 | Speeg et al. |
| 2008/0208194 A1 | 8/2008 | Bickenbach |
| 2008/0214955 A1 | 9/2008 | Speeg et al. |
| 2008/0215056 A1 | 9/2008 | Miller et al. |
| 2008/0221443 A1 | 9/2008 | Ritchie et al. |
| 2008/0221444 A1 | 9/2008 | Ritchie et al. |
| 2008/0221478 A1 | 9/2008 | Ritchie et al. |
| 2008/0221479 A1 | 9/2008 | Ritchie et al. |
| 2008/0221480 A1 | 9/2008 | Hibner et al. |
| 2008/0228104 A1 | 9/2008 | Uber et al. |
| 2008/0232604 A1 | 9/2008 | Dufresne et al. |
| 2008/0234715 A1 | 9/2008 | Pesce et al. |
| 2008/0281225 A1 | 11/2008 | Spero et al. |
| 2008/0306406 A1* | 12/2008 | Thompson ............. A61B 90/39 600/567 |
| 2008/0308607 A1 | 12/2008 | Timm et al. |
| 2009/0015208 A1 | 1/2009 | White et al. |
| 2009/0030405 A1 | 1/2009 | Quick et al. |
| 2009/0048532 A1 | 2/2009 | Stephens et al. |
| 2009/0048533 A1 | 2/2009 | Miller |
| 2009/0062624 A1 | 3/2009 | Neville |
| 2009/0082695 A1 | 3/2009 | Whitehead |
| 2009/0087249 A1 | 4/2009 | Flagle et al. |
| 2009/0088666 A1 | 4/2009 | Miller et al. |
| 2009/0112118 A1 | 4/2009 | Quick, Jr. et al. |
| 2009/0125062 A1 | 5/2009 | Amin |
| 2009/0137927 A1 | 5/2009 | Miller |
| 2009/0146609 A1 | 6/2009 | Santos |
| 2009/0171242 A1 | 7/2009 | Hibner |
| 2009/0171243 A1 | 7/2009 | Hibner et al. |
| 2009/0200042 A1 | 8/2009 | Emerson |
| 2009/0204022 A1 | 8/2009 | Schwindt |
| 2009/0281453 A1 | 11/2009 | Tsonton et al. |
| 2010/0030020 A1 | 2/2010 | Sanders et al. |
| 2010/0063416 A1 | 3/2010 | Cicenas et al. |
| 2010/0152610 A1 | 6/2010 | Parihar et al. |
| 2010/0152611 A1 | 6/2010 | Parihar et al. |
| 2010/0160820 A1 | 6/2010 | Weikel, Jr. et al. |
| 2010/0160823 A1 | 6/2010 | Parihar et al. |
| 2010/0160824 A1 | 6/2010 | Parihar et al. |
| 2010/0185179 A1* | 7/2010 | Chan .................. A61B 17/3478 604/508 |
| 2010/0222700 A1 | 9/2010 | Hibner |
| 2010/0292607 A1 | 11/2010 | Moore et al. |
| 2010/0312140 A1 | 12/2010 | Smith et al. |
| 2010/0317995 A1 | 12/2010 | Hibner et al. |
| 2010/0317997 A1 | 12/2010 | Hibner et al. |
| 2010/0317998 A1 | 12/2010 | Hibner et al. |
| 2010/0324449 A1 | 12/2010 | Rostaing et al. |
| 2011/0004119 A1 | 1/2011 | Hoffa et al. |
| 2011/0084109 A1 | 4/2011 | Ford et al. |
| 2011/0105946 A1 | 5/2011 | Sorensen et al. |
| 2011/0152715 A1 | 6/2011 | Delap et al. |
| 2011/0160611 A1 | 6/2011 | Ritchart et al. |
| 2011/0224577 A1 | 9/2011 | Park |
| 2012/0080332 A1 | 4/2012 | Shelton, IV et al. |
| 2012/0191009 A1 | 7/2012 | Hoon et al. |
| 2012/0215130 A1 | 8/2012 | Field et al. |
| 2013/0289441 A1 | 10/2013 | Videbaek et al. |
| 2014/0171825 A1* | 6/2014 | Eller .................. A61B 10/0233 600/562 |
| 2014/0358032 A1 | 12/2014 | Videbaek et al. |
| 2014/0371585 A1 | 12/2014 | Thompson et al. |
| 2015/0018712 A1 | 1/2015 | Seiger et al. |
| 2015/0073301 A1 | 3/2015 | Videbaek et al. |
| 2015/0223787 A1 | 8/2015 | Coonahan et al. |
| 2015/0238174 A1 | 8/2015 | Reuber et al. |
| 2016/0022251 A1 | 1/2016 | Chudzik et al. |
| 2016/0256138 A1 | 9/2016 | Videbaek et al. |

(56) References Cited

U.S. PATENT DOCUMENTS

| | | |
|---|---|---|
| 2016/0317133 A1 | 11/2016 | Orts et al. |
| 2016/0367229 A1 | 12/2016 | Jorgensen et al. |
| 2016/0367230 A1 | 12/2016 | Almazan |
| 2016/0374650 A1 | 12/2016 | Heske et al. |
| 2017/0042517 A1 | 2/2017 | Heske et al. |
| 2017/0181732 A1 | 6/2017 | Videbaek et al. |
| 2017/0245840 A1 | 8/2017 | Chudzik et al. |
| 2017/0258458 A1 | 9/2017 | Seiger et al. |
| 2018/0125467 A1 | 5/2018 | Reuber et al. |

FOREIGN PATENT DOCUMENTS

| | | | |
|---|---|---|---|
| DE | 3924291 | A1 | 1/1991 |
| DE | 4041614 | C1 | 10/1992 |
| DE | 3924291 | C2 | 7/2000 |
| DE | 10034297 | A1 | 4/2001 |
| DE | 10026303 | A1 | 2/2002 |
| DE | 20204363 | U1 | 5/2002 |
| DE | 20209525 | U1 | 11/2002 |
| DE | 10235480 | A1 | 2/2004 |
| EP | 0433717 | A1 | 6/1991 |
| EP | 0890339 | A1 | 1/1999 |
| EP | 3970658 | A1 | 1/2000 |
| EP | 0995400 | A1 | 4/2000 |
| EP | 1074271 | A2 | 2/2001 |
| EP | 1520518 | A2 | 4/2005 |
| EP | 1579809 | A1 | 9/2005 |
| EP | 1604615 | A1 | 12/2005 |
| EP | 1665989 | A2 | 6/2006 |
| EP | 1829487 | A1 | 9/2007 |
| EP | 2095772 | A1 | 9/2009 |
| EP | 2106750 | A2 | 10/2009 |
| EP | 1569561 | B1 | 10/2010 |
| FR | 1345429 | A | 12/1963 |
| FR | 2739293 | A1 | 4/1997 |
| GB | 2018601 | A | 10/1979 |
| JP | 1-126957 | A | 9/1987 |
| JP | H10508504 | A | 8/1998 |
| JP | 2005530554 | A | 10/2005 |
| JP | 2006509545 | A | 3/2006 |
| JP | 2006528907 | A | 12/2006 |
| JP | 2007502159 | A | 2/2007 |
| WO | 9207500 | A2 | 5/1992 |
| WO | 9508945 | A2 | 4/1995 |
| WO | 9628097 | A1 | 9/1996 |
| WO | 9734531 | A1 | 9/1997 |
| WO | 9825522 | A1 | 6/1998 |
| WO | 9831285 | A1 | 7/1998 |
| WO | 9835615 | A1 | 8/1998 |
| WO | 9846290 | A1 | 10/1998 |
| WO | 9933501 | A1 | 7/1999 |
| WO | 9004832 | A1 | 2/2000 |
| WO | 0030546 | A1 | 6/2000 |
| WO | 0059378 | A2 | 10/2000 |
| WO | 0172230 | A1 | 10/2001 |
| WO | 0222023 | A1 | 3/2002 |
| WO | 0232318 | A1 | 4/2002 |
| WO | 02069808 | A2 | 9/2002 |
| WO | 2005013830 | A1 | 2/2005 |
| WO | 2006015302 | A1 | 2/2006 |
| WO | 2007047128 | A1 | 4/2007 |
| WO | 2007095330 | A2 | 8/2007 |
| WO | 2007112751 | A2 | 10/2007 |
| WO | 2008021687 | A1 | 2/2008 |
| WO | 2008040812 | A1 | 4/2008 |
| WO | 2008131362 | A2 | 10/2008 |
| WO | 2010107424 | A1 | 9/2010 |
| WO | 2010120294 | A1 | 10/2010 |
| WO | 2011019343 | A1 | 2/2011 |
| WO | 2013158072 | A1 | 10/2013 |
| WO | 2014153410 | A1 | 9/2014 |

\* cited by examiner

BIOPSY DEVICE

CROSS-REFERENCE TO RELATED APPLICATIONS

This application is a continuation of U.S. patent application Ser. No. 14/772,994, filed Sep. 4, 2015, which is a U.S. national phase of International Application No. PCT/US2014/031224, filed Mar. 19, 2014, which claims priority to U.S. provisional patent application Ser. No. 61/803,626 entitled "Improved biopsy device" filed Mar. 20, 2013, which is incorporated herein by reference.

BACKGROUND OF THE INVENTION

1. Field of the Invention

The present invention relates to a biopsy device for obtaining tissue samples from human or animal tissue. The invention is particularly, but not exclusively, aimed at percutaneous biopsy, in which it is desirable to gain access to suspect tissue mass in a minimally invasive manner. The invention relates to a biopsy device that is optimized for the sampling of tissues that are resilient and difficult to cut using conventional approaches. Furthermore, a biopsy device is disclosed that is optimized to deliver the highest possible tissue yield.

2. Description of the Related Art

For diagnostic purposes it may be desirable to obtain a tissue sample of a human or animal body for cytological or histological in vitro examination. The tissue sample can be examined for specific qualities based on which a diagnosis can be made and therapy can be administered. For the harvesting of tissue samples, several approaches exist. The conventional open biopsy is increasingly being replaced by less-invasive biopsy methods, and especially the field of breast biopsy has seen rapid development of novel biopsy device types that reduce the invasiveness of the tissue sampling procedure.

In the percutaneous technique, a needle is used to gain access to the suspect tissue mass in a less invasive fashion. This needle may be hollow, permitting the aspiration of single cells and tissue fragments into a lumen by application of a vacuum (aspiration biopsy). Alternatively, larger tissue cores may be harvested by means of a needle containing an inner movable trocar with a notch formed to receive tissue cores, and an outer, slidable cutting cannula with a sharpened distal end used to sever these cores from the surrounding tissue (core needle biopsy). By advancing the inner trocar into a suspect lesion and subsequently advance the outer slidable cannula to cover the notch completely, a tissue sample may be severed and held in the notch. The needle may then be retracted from the body of the patient, and the tissue sample may be collected and stored for further analysis.

Several parameters define whether a tissue sample is useful for analysis, and one of the more important is the sample size. Core needles, while representing a less-invasive approach to tissue sampling, are often incapable of delivering samples of an adequate size for reliable diagnosis. Using vacuum to engage and draw tissue towards the sample notch can significantly increase tissue sample sizes for a given biopsy needle diameter thereby improving diagnostic accuracy. Another well-known technique to increase sample size is to harvest multiple samples in order to obtain sufficient tissue for a reliable diagnosis. Instead of multiple insertions biopsy systems have been developed that enable the extraction of multiple samples with a single biopsy device insertion, the so called SIMS biopsy devices: "Single Insertion—Multiple Samples". These devices are typically vacuum assisted and may include a tissue-collecting portion that can be moved from an advanced position at the sampling site to a retracted position where the tissue sample may be collected. Exemplary SIMS biopsy devices are disclosed in prior art documents WO 2006/005342, WO 2006/005343, WO 2006/005344 and WO 2006/005345 employing a spring-loaded linear cutting cannula.

SUMMARY OF THE INVENTION

In a first aspect the present disclosure relates to a biopsy device for harvesting at least one tissue sample from a suspect tissue mass in a body of a living being, comprising a cutting cannula that is hollow, an inner member comprising a sharpened distal tip configured to be introduced into the body and a sample notch for receiving the at least one severed tissue sample, the inner member receivable in the cutting cannula, and a cutting mechanism configured for causing the cutting cannula to be longitudinally displaced in a distal direction from a first position at the proximal end of the sample notch exposing the sample notch, to a second position at the distal end of the sample notch, so as to sever said tissue sample from remaining body tissue at the harvesting site.

In one embodiment of the invention the inner member is a rigid and/or rotatable toothed rack that is longitudinally displaceable in the cutting cannula between a first advanced position in which the sample notch of the toothed rack projects from the distal end portion of the cutting cannula, and a second retracted position in which the sample notch is in a proximal position with respect to the distal end portion of the cutting cannula in which the at least one tissue sample can be transferred from said sample notch. The cutting cannula and/or the toothed rack with the sample notch are preferably independently movable in response to directions from a user of the biopsy device. A transport mechanism, e.g. in the form of an actuator system, may be provided to move the toothed rack. The transport mechanism may comprise a toothed wheel configured for engagement with the toothed rack.

In a further embodiment of the invention the inner member forms a hollow needle wherein the biopsy device is configured to longitudinally displace a severed tissue sample inside the hollow needle in a proximal direction from the sample notch to a collection position where the tissue sample can be collected, e.g. transferred into a tissue collection tank. The longitudinal displacement may be provided by means of a vacuum delivered through the hollow needle.

The biopsy device according to the invention is preferably adapted for being handheld by the user during harvesting of a tissue sample.

A further embodiment of the invention relates to a disposable unit for a biopsy device for harvesting at least one tissue sample from a suspect tissue mass in a body of a living being comprising a cutting cannula that is hollow, an inner member comprising a sharpened distal tip configured to be introduced into the body and a sample notch for receiving the at least one severed tissue sample, the inner member receivable in the cutting cannula, and a cutting mechanism configured for causing the cutting cannula to be longitudinally displaced in a distal direction from a first position at the proximal end of the sample notch exposing the sample notch, to a second position at the distal end of the sample notch, so as to sever said tissue sample from remaining body tissue at the harvesting site. The disposable unit may further comprise an interface for connecting the disposable unit to a handle unit.

BRIEF DESCRIPTION OF THE DRAWINGS

The invention will be described in further detail with reference to the drawings in which:

FIG. 8a shows a tissue collection tank.

FIG. 8b is a cut through illustration of the tissue collection tank in FIG. 8a.

Corresponding reference characters indicate corresponding parts throughout the several views. The exemplifications set out herein illustrate embodiments of the invention and such exemplifications are not to be construed as limiting the scope of the invention in any manner.

DETAILED DESCRIPTION OF THE INVENTION

Figure 1:
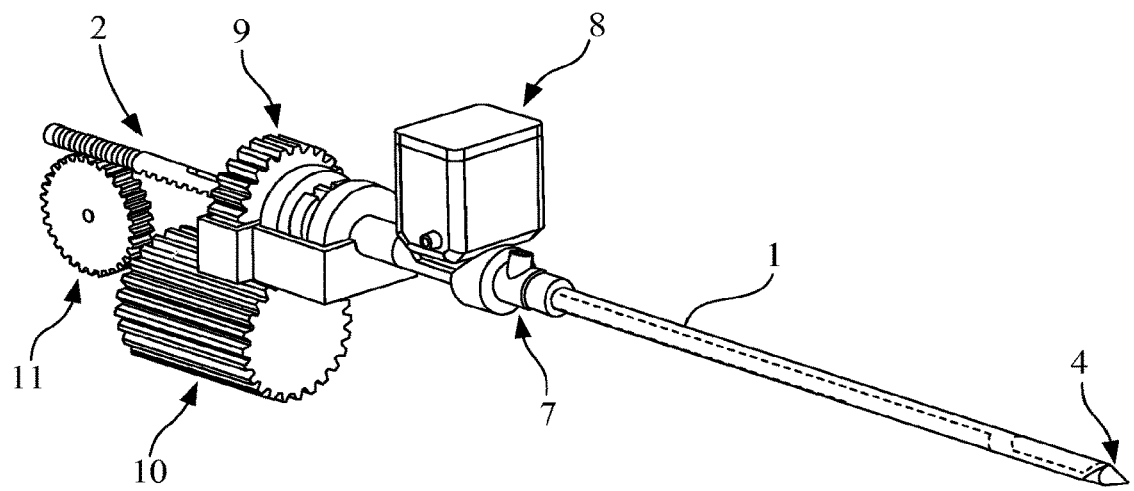
FIG. 1 is an exemplary embodiment of a biopsy device according to the invention.
Figure 2:
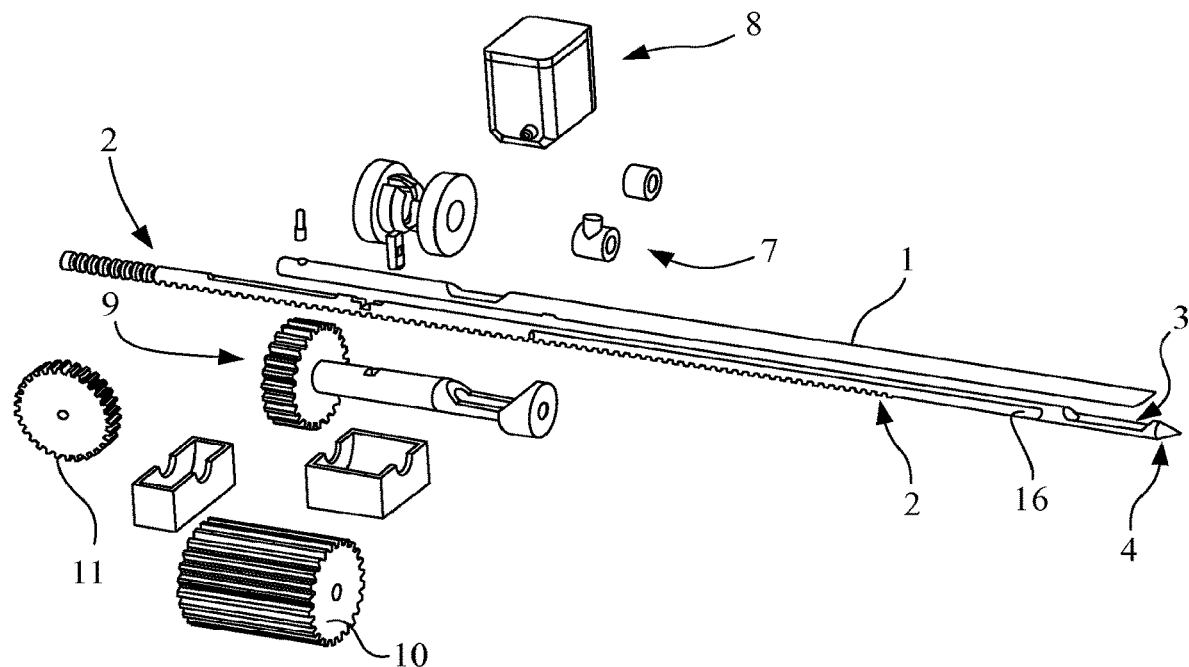
FIG. 2 is an exploded view of the components in FIG. 1.
Figure 3:
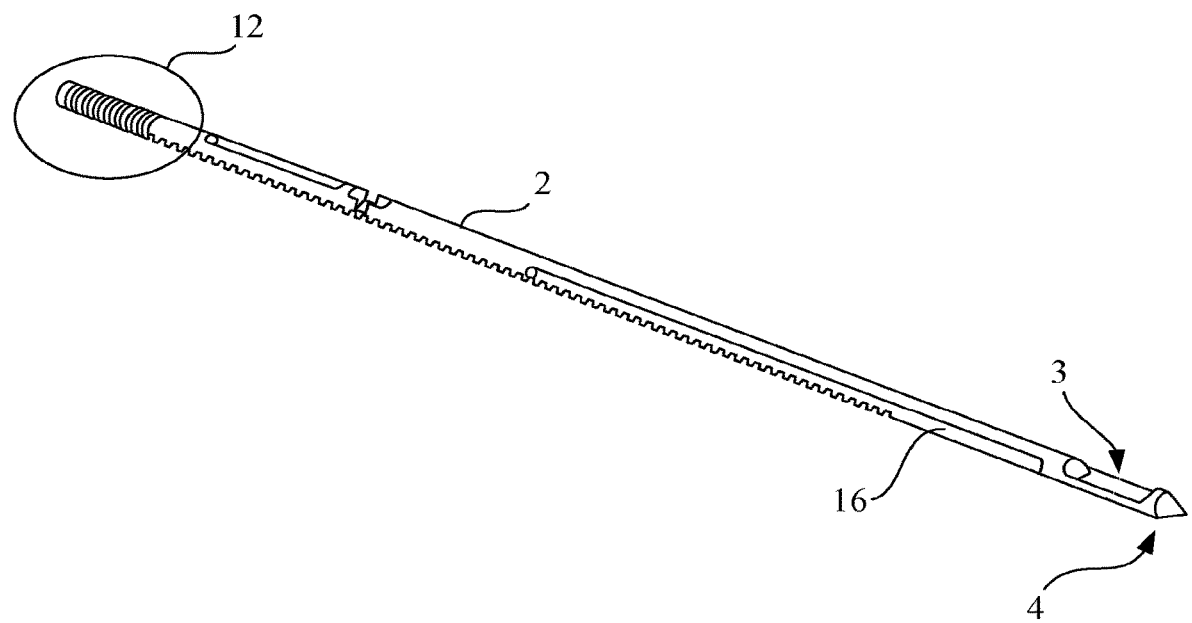
FIG. 3 is a detailed view of a rigid toothed rack with a sharpened tip and sample notch at the distal end and a rotation zone in the proximal end.
Figures 4A, 4B:
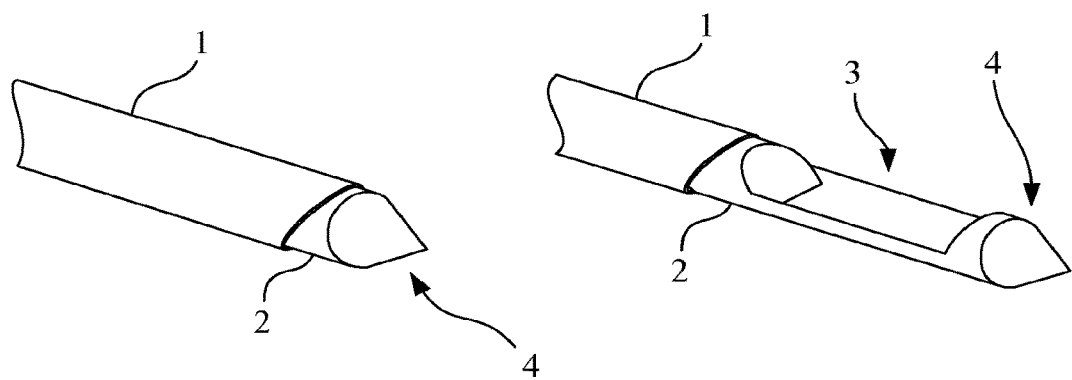
FIG. 4a shows a cutting cannula in an advanced position covering a sample notch.
FIG. 4b shows a cutting cannula in a retracted position exposing a sample notch.

The drawings illustrate exemplary biopsy devices which are provided with a needle portion comprising a cutting cannula 1, 1' and a sample notch 3 with a sharpened distal tip 4 for piercing tissue. The cutting cannula 1 is provided with a slanted cutting profiled as illustrated e.g. in FIGS. 2 and 6, whereas the cutting cannula 1' is provided with a straight cutting profile 24 as illustrated e.g. in FIGS. 5, 7 and 9. The sample notch 3 is part of a rigid toothed rack 2, and is movable between a first advanced and a second retracted position when actuated by a suitable source of mechanical motion. The source of mechanical motion may be a motor that may be powered by a battery and operatively connected to the rigid toothed rack 2 by means of one or more gear wheels 11.

The operative connection between the rigid toothed rack 2 and the gear wheels 11 is configured to permit full 360 degree rotation of the toothed rack 2, including the sample notch 3, about its longitudinal axis. Such rotation may for instance be permitted by providing a proximal rotation zone 12 with a series of cut-outs that run around the entire circumference of the toothed rack. A rotation control gear 9, that is in operative connection with the rigid toothed rack, is engaged by a rotation driver gear 10 to support the rotation of the rigid toothed rack 2 about its longitudinal axis. Another set of gearwheels may be in operative engagement with the cutting cannula 1 to provide full 360-degree rotation of the cutting cannula 1 either independently or in step with the rotation of the rigid toothed rack 2.

The cutting cannula 1, 1' may be retracted when actuated by a suitable source of mechanical motion. In the first embodiment, the source of mechanical motion may be a second motor that is powered by a battery and operatively connected to the cutting cannula 1, 1' by means of a series of gears driving an actuator rod. Retraction of the cutting cannula 1, 1' exposes the sample notch 3, 3', and permits tissue to prolapse into the lateral opening of the sample notch 3, 3'.

During or after retraction of the cutting cannula 1, 1', a vacuum may be switched on to support the prolapsing of tissue into the sample notch 3, 3'. Vacuum is communicated from a vacuum pump and a hose through a vacuum gasket 7 that is in operative connection with the cutting cannula 1, 1' and into the inner lumen of cutting cannula 1, 1'. The rigid toothed rack 2 is provided with at least one vacuum cut-out 16 that run along the length of the rigid toothed rack 2, and end in sample notch 3, and the vacuum from the vacuum pump is communicated through these vacuum cut-outs 16 to the sample notch 3 as soon as the pump is turned on.

A vacuum accumulator/reservoir may be configured to build and store a vacuum, is also in fluid communication with the sample notch 3, 3', and may provide a transient boost to the vacuum strength immediately prior to firing of the cutting cannula 1, 1' to increase sample size.

Retraction of the cutting cannula 1, 1' cocks a spring-loaded firing mechanism that is capable of powering the cutting cannula forward (i.e. in a distal direction) at high speed. As the cutting cannula 1, 1' moves forward at high speed, the sharpened distal end of the cannula 1, 1' makes contact with the tissue that has prolapsed into the sample notch 3, 3' and severs it from the surrounding connecting tissue.

Figure 5:
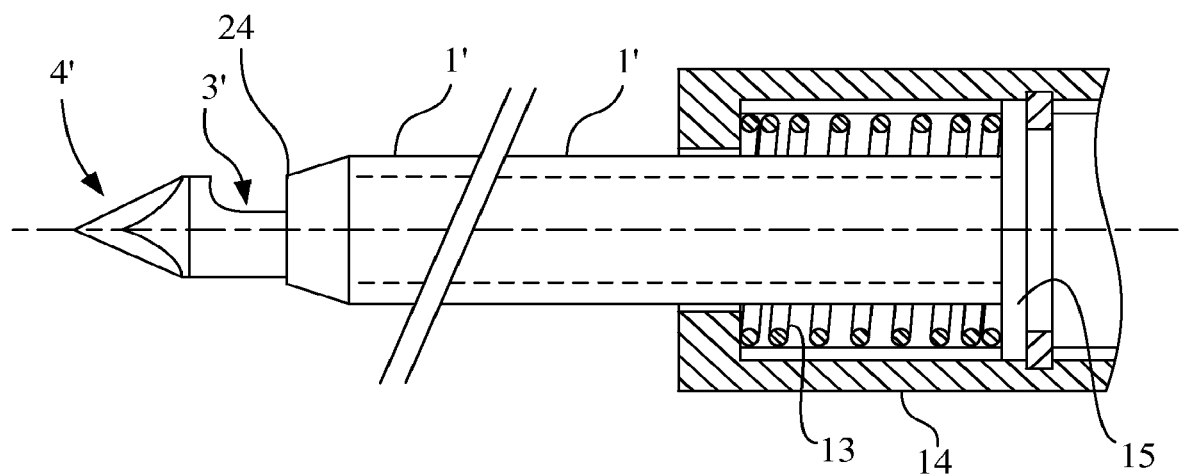
FIG. 5 shows a damper spring for use in connection with overshoot of a spring-loaded cutting cannula.

As illustrated in FIG. 5 the cutting cannula 1' may be permitted to continue its travel by a damper spring 13 that is placed in a damper spring housing 14 and is in operative connection with a rear flange 15 of the cutting cannula 1'. The inertia of the cutting cannula 1' will allow it to proceed 1-2 mm beyond the permissible traveling distance of the spring-loaded firing mechanism, and will ensure that the sharpened distal end of the cutting cannula 1' has achieved a suitable overlap with the distal section of the sample notch 3'. Following the overthrow, the damper spring 13 ensures that the cutting cannula 1' is returned to its neutral position in preparation for the next tissue sample.

Figure 6:
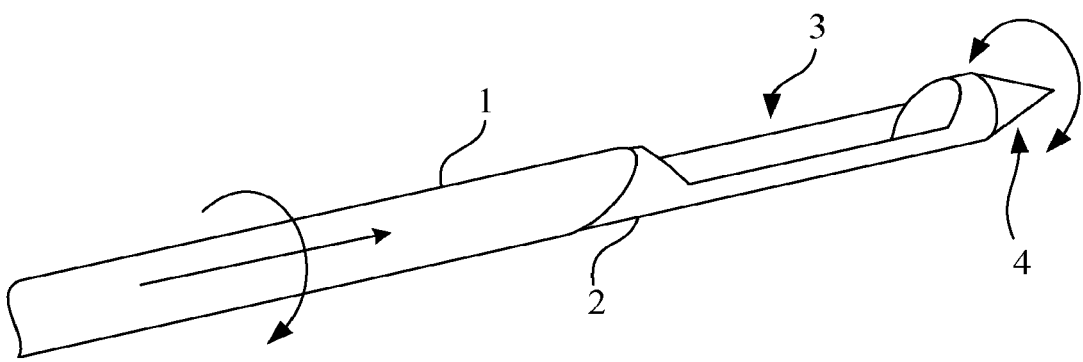
FIG. 6 shows a counter-rotation cutting interface between a sample notch and a cutting cannula.

As illustrated in FIG. 6 the user of the biopsy device has the option of rotating the toothed rack 2 with the sample notch 3 relative to the stationary cutting cannula 1 to sever any connective tissue that has not been completely severed by the cutting cannula 1. Connective tissue that has not been completely severed may restrict retraction of the tissue sample and cause pain to the patient. The rotation causes connective tissue that has not been completely severed to saw against the sharpened distal end of cutting cannula 1 for as long as needed to complete the severing. Rotation may be step-wise and may interchange between a clockwise and a counter-clockwise direction and take place over a rotation angle of e.g. +1-20 degrees relative to a neutral position. Furthermore the cutting cannula 1 may be retracted and advanced in steps of 1-2 mm during rotation to further support the severing of tissue. When unrestricted movement of the sample notch 3 has been restored, the toothed rack 2 may continue its motion from the first advanced to the second retracted position to transport the tissue sample in sample notch 3 out of the body of the patient.

Figures 8A, 8B:
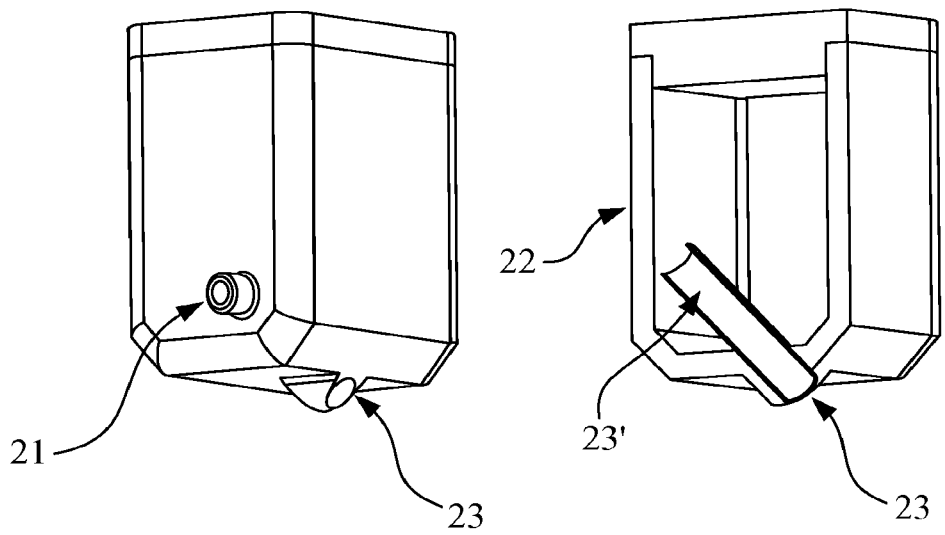

The tissue sample may be collected in a tissue collection tank 8 comprising a vacuum spout 21 through which a vacuum from a vacuum pump or vacuum accumulator may be communicated into a collection tank chamber 22. From the collection tank chamber, the vacuum may be communicated through a tissue collection spout 23 for enhanced collection of the tissue sample. As illustrated in FIG. 8*b* the collection spout 23 forms a collection tube 23' inside the collection tank 22 extending with a certain length from the bottom of the tank 22. Following collection of the tissue sample from the sample notch 3, said sample notch 3 may be returned to the sampling site for collection of the next tissue sample.

Figure 7:
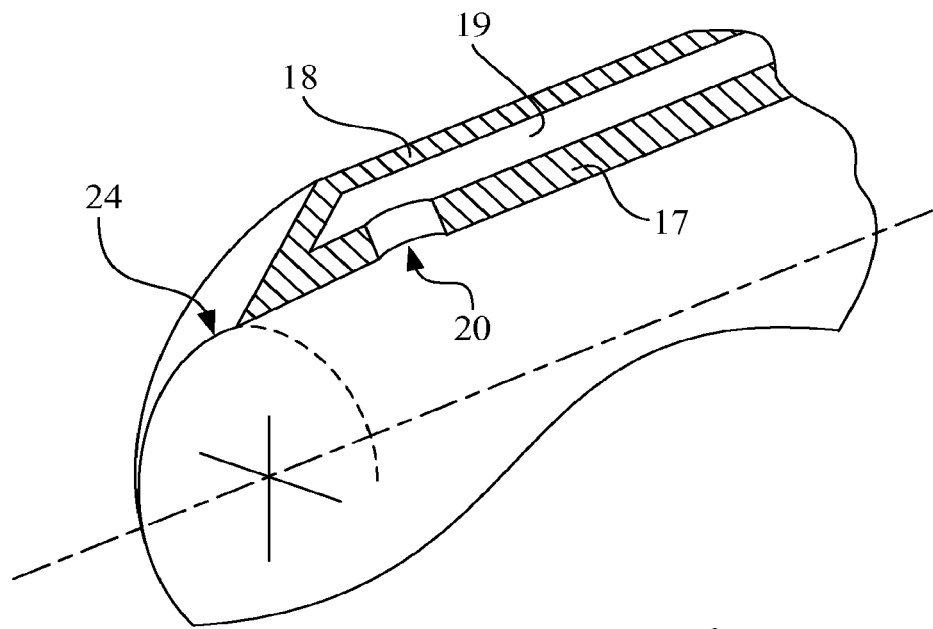
FIG. 7 is a cross-sectional view of a cutting cannula featuring a longitudinal air channel having a lateral vent hole.
Figure 9:
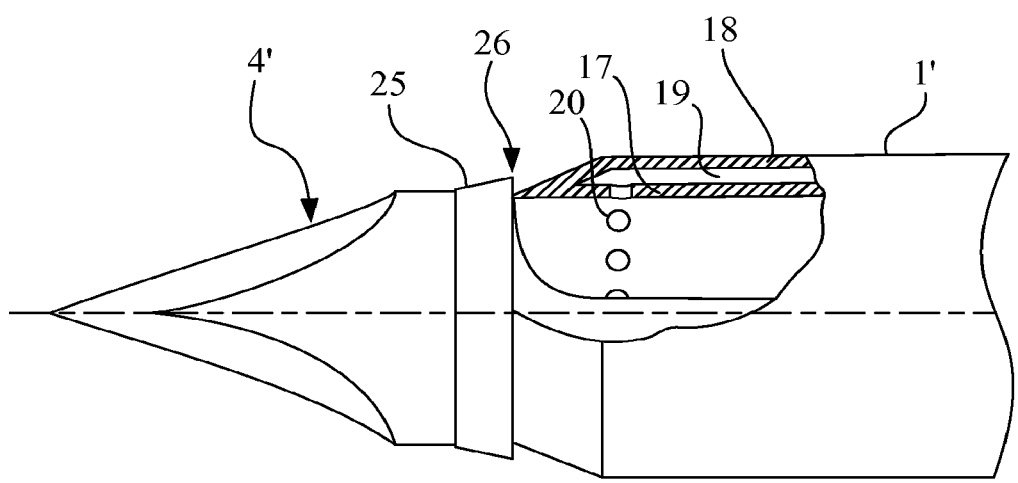
FIG. 9 illustrates the cutting interface between a cutting cannula and a protrusion at the inner member forming a cutting board for the cutting cannula. A cut-out in the drawing shows the longitudinal air channel and a plurality of vent holes in the cutting cannula.

As illustrated in FIGS. 7 and 9 the cutting cannula may have an inner tube 17 and an outer tube 18 forming between them a longitudinal air channel 19 that is at a proximal end in fluid communication with a first vacuum pump through a two-way valve that may be switched between a vacuum position and a position that permits entry of atmospheric air into the air channel. At the distal end the air channel 19 is in fluid communication with the lateral opening of the sample notch 3 through at least one vent hole 20 that is formed in the inner tube 17.

As illustrated in FIG. 9 a plurality of the vent holes 20 may be distributed circumferentially around the inside of the inner tube 17. As illustrated in FIG. 9 a protrusion 25 formed as a collar may be provided adjacent to the sharpened distal end 4'. The interface 26 between the protrusion 25 and the cutting cannula 1' forms a cutting board to ensure that connective tissue is cut properly during severing.

A frequently encountered complication in the harvesting of tissue samples is the presence of fibrous or connective tissue. Such tissue is characterized by being highly resilient and difficult to cut. The typical manifestation of malfunctions related to connective tissue is that the biopsy device gets stuck in the body of the patient and has to be removed by force or surgical intervention. This may be stressful to both physician and patient and may additionally be very painful for the patient. Inadequately severed connective tissue is a known problem for all kinds of biopsy devices and the problem is highly undesirable.

The use of a linear cutter requires a very precise interplay between the sharpened distal end of the cutting cannula and the distal section of the sample notch if appropriate severing of connective tissue is to occur. For this reason it is important that the position of the sample notch is very precisely controlled relative to the position of the cutting cannula. SIMS devices featuring a linear, spring-loaded cutting cannula typically employ a sample notch that is attached to a flexible bendable elongate member (e.g. a non-rigid toothed rack), and this toothed rack may not always produce the desired control of position of the sample notch due to the flexibility, design and material chosen. Some prior art devices employ toothed racks made of thermoplastic elastomers with significant longitudinal elasticity. By having the sample notch in a rigid toothed rack, which is longitudinally inelastic, a better control of position is provided. Thereby an appropriate overlap of the sharpened end of the cutting cannula with the distal section of the sample notch can be provided. Failure to establish a precise position of the sample notch may result in the incomplete closing of the sample notch opening. A rigid toothed rack provides the necessary lateral inelasticity and stability to ensure that the sharpened distal end of the cutting cannula completely closes the opening of the sample notch. Employing a rigid toothed rack therefore provides an improved control of the longitudinal and lateral position of the distal sharpened end of the cutting cannula relative to the distal section of a sample notch.

In one embodiment the proximal end of the rigid toothed rack is configured to operatively connect with a retraction gear wheel, and is furthermore configured to permit 360 degree rotation of the toothed rack about its longitudinal axis without requiring that the operative connection with the retraction gearwheel is interrupted. This may be provided by means of a rotation mechanism.

In a further embodiment of the invention the rigid toothed rack comprises a rotation zone in the proximal end with circumferential teeth, e.g. in the form of a series of cut-outs that run around the entire circumference of the toothed rack, thereby permitting rotation of the rigid toothed rack. The rigid toothed rack may be rotatable within the cutting cannula and/or the rigid toothed rack and the cutting cannula are rotatable simultaneously relative to the biopsy device. The permitted rotation may be 360 degrees. The biopsy device may further comprise a rotation control gear attached to the rigid toothed rack. A rotation driver gear may be provided and configured to engage with the rotation control gear for rotation of the rigid toothed rack. The cutting cannula may also be configured to rotate, such as 360 degrees, about its longitudinal axis.

In a further embodiment of the invention the rigid toothed rack is configured such that longitudinal displacement of the rigid toothed rack to the second retracted position can only be provided in a predefined rotational orientation of the rigid toothed rack. Thus, the rigid toothed rack may be rotatable within the cutting cannula only in the first advanced position, and/or the rigid toothed rack and the cutting cannula are rotatable simultaneously relative to the biopsy device only in the first advanced position.

Whether the rigid toothed rack and/or the cutting cannula is rotated simultaneously or independently may at least partly be controlled by means of an interlock mechanism configured for fixing the rigid toothed rack and the cutting cannula relative to each other. E.g. the interlock mechanism may have two states, one state that allows free movement of the cutting cannula and the toothed rack relative to each other and one state that fixes the two to each other.

This may help to ensure that the sample notch is always oriented correctly with respect to a tissue collection tank when a tissue sample is transferred to the tank. This may be provided if the toothing of the toothed rack is only located at one side of the rigid toothed rack. If there is a proximal rotation zone of the toothed rack as mentioned above, the toothing that extends in the distal direction beyond the rotation zone is only located at one side of said rigid toothed rack. A control system may help to ensure that the rigid toothed rack has the correct rotational orientation before retracting to the retracted position.

Rotation of the rigid toothed rack relative to the cutting cannula (or vice versa) may be advantageous during severing of a tissue sample and may thereby be an improvement of the cutting mechanism. Rotation of the toothed rack, and thereby the sample notch, relative to the cutting cannula with the sharpened distal end, may result in a "sawing" motion that may complete the severing of incompletely severed connective tissue. Counter-rotation of the cutting cannula and the rigid toothed rack may further be provided during cutting which allows for enhanced cutting of e.g. connective tissue.

Thus, in one embodiment of the invention the rigid toothed rack is rotatable within the cutting cannula during severing of the at least one tissue sample. The cutting mechanism may be configured to rotate the rigid toothed rack within the cutting cannula during severing of the at least one tissue sample. The rotation may be either stepwise or continuous. The rigid toothed rack and/or the cutting cannula may be rotatable in clockwise and/or in counter-clockwise directions. During severing the rotation angle of the rigid toothed rack relative to the cutting cannula may oscillate between −5 and +5 degrees during severing, more preferably between −10 and +10 degrees, more preferably between −15 and +15 degrees, more preferably between −20 and +20 degrees, more preferably between −25 and +25 degrees, more preferably between −30 and +30 degrees, i.e. like a sawing motion oscillating between clock-wise and counter clock-wise directions.

When taking a biopsy it is often necessary to rotate the entire biopsy device inside the patient in order to position the sample notch against the suspect tissue mass. This may lead to awkward handling situations during harvesting of tissue samples. A further advantage of rotational capability is therefore that the rigid toothed rack and the cutting cannula can be rotated simultaneously, preferably controlled by the user, about their longitudinal axis relative to the biopsy device in order to orientate the sample notch towards the suspect tissue mass, e.g. prior to activation of the firing mechanism. Thus, the biopsy device can be held in a steady position while the rigid toothed rack and the cutting cannula are rotated into the correct angular orientation relative to the suspect tissue mass.

Another way to enhance the correct severing of tissue is if the cutting mechanism is configured to interchangeably retract and advance the cutting cannula in small longitudinal steps during severing of a tissue sample. The size of the steps may between 0 and 3 mm, or between 0 and 1 mm, or between 1 and 2 mm or between 2 and 3 mm. This corresponds to a sawing motion in the longitudinal direction.

The cutting mechanism may also be improved if it is configured to provide a predefined overlap and/or overshoot during severing of a tissue sample such that the distal end of the cutting cannula passes beyond the distal end of the sample notch temporarily before returning to said second position. The length of said overshoot may be between 0.5 and 5 mm, or between 0.5 and 1 mm, or between 1 and 2 mm, or between 2 and 3 mm, or between 3 and 4 mm, or between 4 and 5 mm. This overshoot of the cutting cannula may help to apply further stress to incompletely severed tissue. The overshoot may be provided by means of an elastic element provided in connection with the cutting cannula. One solution could be in the form of at least one damper spring mounted in a damper spring housing. The damping may also be provided by using a damping element formed in rubber. The elastic element may be configured to work along with a firing mechanism of the cutting cannula effected during severing of a tissue sample. If the firing mechanism is stopped by the elastic element the inertia of the cutting cannula and the elasticity of the elastic element will allow the sharpened end of the cutting cannula to proceed a certain length beyond the traveling distance of the spring-loaded firing mechanism, and thereby ensure that the sharpened distal end of the cutting cannula achieves a suitable overlap with the distal section of the sample notch. Subsequent to this overshoot, the elastic element ensures that the cutting cannula can be returned to its neutral position in preparation for the next tissue sample.

As an alternative, or supplement to, an overlap or overshoot between the distal sharpened end of the cutting cannula and the distal section of the sample notch, the inner member may further comprise a circumferential protrusion and/or collar located between the sharpened distal end and the sample notch, said circumferential protrusion formed to match the distal end of the cutting cannula. The circumferential protrusion may thus be configured to form a cutting surface for the cutting cannula during severing of a tissue sample. The cutting board (protrusion) may be disposed about the outer periphery of the sample notch and serve the purpose of ensuring that the tissue sample is completely and cleanly severed by the cutting cannula. The cutting mechanism may be configured such that the cutting cannula and the circumferential protrusion encounter during severing of a tissue sample. The protrusion is then preferentially formed in a material that is softer than the cutting cannula in order not to blunt the cutting cannula and preserve the sharpness of the cutting cannula. The cutting mechanism may alternatively be configured such that the cutting cannula and the circumferential protrusion does not encounter during severing of a tissue sample. Thus, the circumferential protrusion may be brought into close proximity without encountering during severing of a tissue sample. I.e. direct physical contact between the protrusion and the sharpened distal end of the cutting cannula is avoided but established at the material surface in close proximity to said sharpened distal end. With such a protrusion the transport of the tissue sample must be provided through the inside of the inner member, typically by means of vacuum, if SIMS functionality is desired.

In a further embodiment of the invention the cutting cannula comprises at least one longitudinal vacuum channel (aka longitudinal air channel or passage) formed inside the external shell/wall of the cutting cannula. The longitudinal vacuum channel may be circumferential. This air channel may be provided by forming the cutting cannula as an inner and an outer tube forming between them an air passage that runs longitudinally along the length of the inner and outer tube. Fluid communication from this air channel and into the inner lumen of the cutting cannula may be provided by one or more lateral vent holes extending from the inside of the cutting cannula to the longitudinal air channel A plurality of said lateral vent holes may be distributed circumferentially in the cutting cannula. The longitudinal vacuum channel may then, in its distal end, be in fluid communication with the sample notch when the rigid toothed rack is in its first advanced position. Thereby the cutting cannula may be configured such that a vacuum or air flow can be provided and/or established inside the cutting cannula, e.g. an airflow from the air channel and into the inner lumen of the cutting cannula. Fluid communication from this air channel and to the external of the cutting cannula may be provided by at least one vacuum spout and may be controlled by at least one vacuum valve. A vacuum pump may then be connected to the air channel via this vacuum valve, in which case a vacuum may be communicated through the air channel and the air vent holes and into the inner lumen of the cutting cannula. Thus, air may be sucked out of the inner lumen of the cutting cannula. Such evacuation may be useful for reducing or eliminating problems with air that has been accidentally introduced in the biopsy cavity and disturbs image quality in an ultrasound-guided biopsy procedure. Unwanted air may be introduced in the biopsy cavity when the rigid toothed rack is being advanced from the second retracted position and to the first advanced position. This advancement of the rigid toothed rack inside the cutting cannula may function as a piston that compresses the air inside the cutting cannula and this air is consequently blown into the biopsy cavity disturbing the ultrasound picture. If air is evacuated from the cutting cannula through the longitudinal vacuum channel inside the sidewall of the cutting cannula during advancement of the rigid toothed rack this problem can be addressed and solved.

A further embodiment of the invention comprises a tissue collection tank for collecting the at least one tissue sample transferred from the sample notch. The tank may comprise a tissue-collecting spout that may be configured to slide into the sample notch chamber and scoop the tissue sample into a sample tank. To enhance the collection of the tissue sample the tissue collection tank may be configured to be vacuumized, e.g. by connection to a vacuum pump via a vacuum port at the tank. The collecting spout may be elongated to form a pipe (aka collection pipe) to enhance the vacuum assisted collection of a tissue sample into the tank. At the outside the collection spout/pipe forms a small spout but at the inside of the tissue collection tank the collection pipe extends and/or protrudes into the tissue collection tank, i.e. the collection pipe may protrude from the bottom or side of the inside of the tissue collection tank. Thus, the collection pipe has a certain length inside the tissue collection tank. This length of the collection pipe may be at least 2 mm, or at least 4 mm, or at least 6 mm, or at least 8 mm, or at least 10 mm, or at least 12 mm, or at least 14 mm, or at least 16 mm, or at least 18 mm, or at least 20 mm, or at least 22 mm, or at least 24 mm, or at least 26 mm, or at least 28 mm, or at least 30 mm, or at least 32 mm, or at least 34 mm, or at least 36 mm, or at least 38 mm, or at least 40 mm.

Some biopsy devices are constantly connected to external vacuum pumps via external vacuum hoses. These pumps can deliver a powerful and constant vacuum to the biopsy device but the necessary vacuum hoses reduce the manageability of the biopsy device for the user. A solution to that problem has until now been to provide one or more local battery driven small vacuum pumps integrated in the biopsy device. However, such small vacuum pumps can only provide a limited airflow which sometimes is not sufficient to maintain a constant vacuum level. A solution to that problem can be a vacuum reservoir integrated in the biopsy device that can deliver a boost to the (negative) airflow for one or more short periods of time, this additional airflow provided by the vacuum reservoir can thereby maintain a certain vacuum level. The biopsy device can thereby be provided with one or more small vacuum pumps supplied by the vacuum reservoir when necessary. A further embodiment of the invention therefore comprises a vacuum reservoir (aka vacuum accumulator) configured for accumulating a volume of vacuum that can be delivered as a transient boost in the airflow so as to maintain a level of vacuum present in the system. Such a vacuum reservoir can for instance be powered by a battery. The vacuum reservoir may be in fluid communication with the sample notch and configured to provide an increased suction to maintain the vacuum level in the sample notch during severing of a tissue sample, e.g. immediately before release of the cutting cannula in order to increase the amount of tissue that prolapses into the sample chamber and thereby maximize the size of the severed tissue sample. The vacuum reservoir may also be in fluid communication with the inside of the hollow inner member and configured to provide a transient boost of airflow when a tissue sample is being sucked through the inner member. Furthermore, the vacuum reservoir may be in fluid communication with the tissue collection tank and configured to provide a vacuum to or an increased suction in the tissue collection tank to main a vacuum level when a tissue sample is transferred from the sample notch and into the tissue collection tank. The vacuum reservoir may have a volume of 5-100 mL, or 5-10 mL, or 10-20 mL, or 20-30 mL, or 30-40 mL, or 50-100 mL.

Retraction of the cutting cannula to expose the sample notch may for instance be actuated by a motor that is powered by a battery and connected to one or more gearwheels, but other power sources and means of mechanical actuation are also envisioned. This retraction of the cutting cannula may facilitate the cocking of a firing mechanism that may for instance be spring-loaded. Other firing mechanisms, including electric, pneumatic and chemical, may also be provided. The cutting movement of the cutting cannula during the actual severing of tissue may be powered by the energy that is stored in a firing mechanism and happens as a high-speed linear passage across the laterally facing opening of the sample notch. During this passage, the sharpened distal end of the cutting cannula makes contact with the tissue that has prolapsed into the sample notch chamber and severs it from the surrounding tissue, thus creating a tissue sample in the sample notch. The firing mechanism may be replaced with a linear actuator that allows the controlled advancement of the cutting cannula during severing. In this case advancement of the cutting cannula is more controlled and it may be desirable to rotate the cutting cannula during advancement to adequately sever the tissue as described previously.

To provide for SIMS functionality retraction of the sample notch may be provided by means of a motor that is operatively connected to the rigid toothed rack by means of one or more gearwheels. When activated, this motor causes the rigid toothed rack and the sample notch to travel from the first advanced position to the second retracted position, where the sample may be retrieved, e.g. by means of a tissue collection tank, but other means of retrieval—including manual retrieval—may also be envisioned. After completion of sample retrieval, the sample notch may be returned to the sampling site by reversing the direction of rotation of the motor.

The firing mechanism may be configured for causing the cutting cannula and the inner member to be longitudinally displaced in a distal direction, so as to penetrate body tissue at or near the suspect tissue mass prior to the cutting operation when harvesting a sample.

In one embodiment of the invention the inner member comprises a vacuum port in fluid communication with the sample notch. The inner member may thus be configured such that the sample notch can be vacuumized. A vacuum pump may be provided for generating a suction effect in the sample notch to increase the size of the tissue sample that prolapses into the sample notch, the vacuum pump being in fluid communication with the sample notch through a longitudinally extending passage in the inner member.

A further embodiment of the invention comprises a handle unit with a power source and at least one motor for driving the cutting mechanism and the displacement of the inner member and wherein at least the cutting cannula and the inner member are comprised in a disposable unit, which is releasably secured to the handle unit.

To ensure that the cutting cannula and the sample notch achieve an overlap that is sufficient to cleanly sever the tissue to be sampled, the cutting cannula is preferably characterized by very tight length tolerances. Such tolerances may be achieved by the use of materials with low creep that are processed using high-precision milling or molding, and possibly result in total length variations of no more than +/−0.5 mm depending on the overall total length of the cutting cannula. A preferred material for the cutting cannula is stainless steel which is made into tubes. These tubes are typically made by rolling and welding sheet metal to form a tubular structure which is then drawn through a tool with a diamond insert to achieve the desired diameter. Multiple drawings may be employed to achieve high precision. By utilizing stainless steel low creep for the cutting cannula, none or minimal elongation and achievable manufacturing tolerances are possible. Other materials, including titanium, are also envisioned for the making of the cutting cannula.

To further support appropriate overlap between cutting cannula and sample notch, also the rigid toothed rack may be characterized by very tight length tolerances. Such tolerances may in some embodiments be achieved by the use of materials with low creep that are processed using high-precision milling or molding, and possibly result in total length variations of no more than +/−0.5 mm depending on the overall total length of the rigid toothed rack. A preferred material for the rigid toothed rack is stainless steel. The rigid tooted rack would typically be made by milling a turned stainless steel metal rod in order to achieve the desired geometry. Other materials suited for the rigid tooted rack are titanium or similar metals with a high modulus of elasticity. Alternative materials include thermoplastic elastomers with suitable fillers for increased modulus of elasticity. Suitable types for a rigid toothed rack would be LCP (Liquid Crystal Polymer), PEEK (Polyetheretherketone) in any grade. Thermoplastic elastomers have the benefit of being relatively easy to process and manufacture, but they are less rigid and will also tend to creep and shrink more than metal.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A biopsy device for harvesting at least one tissue sample from a suspect tissue mass in a body of a living being, comprising:
   a cutting cannula that is hollow;
   a rotatable inner member rotatable about a longitudinal axis and having a toothed rack, a sharpened distal tip, and a sample notch configured to receive tissue at a site in the body, the inner member configured to be received in the cutting cannula, the toothed rack having a proximal portion defining a rotation zone and a distal portion defining a non-rotation zone, the rotation zone of the toothed rack having circumferential toothing configured as a series of discrete, longitudinally spaced cut-outs that run around an entire circumference of the toothed rack, the circumferential toothing facilitating both a longitudinal movement and a rotational movement of the toothed rack and inner member, and the distal portion having non-circumferential toothing facilitating the longitudinal motion; and
   a drive configured to engage the toothed rack to move the toothed rack within the cutting cannula in the longitudinal movement and the rotational movement, wherein the drive comprises:
   a longitudinal drive gear engaged with the toothed rack and configured to move the toothed rack in the longitudinal movement and configured to traverse both the circumferential toothing and the non-circumferential toothing; and
   a rotational drive gear operatively coupled to the rotatable inner member to move the toothed rack in the rotational movement, wherein the longitudinal drive gear is engaged with the circumferential toothing within the proximal portion during rotational movement, wherein a radial position of the sample notch is controlled via the rotational movement and the longitudinal position of the sample notch is controlled via the longitudinal movement.

2. The biopsy device of claim 1, wherein the toothed rack of the rotatable inner member is a rigid toothed rack, and wherein the rotatable inner member is longitudinally displaceable in the cutting cannula between an advanced position in which the sample notch of the rigid toothed rack projects from a distal end portion of the cutting cannula, and a retracted position in which the sample notch is in a proximal position with respect to the distal end portion of the cutting cannula to facilitate a transfer of a tissue sample from the sample notch.

3. The biopsy device of claim 1, wherein the drive comprises a gear wheel engageable with the toothed rack to longitudinally displace the rotatable inner member in the cutting cannula between an advanced position in which the sample notch projects from a distal end portion of the cutting cannula, and a retracted position in which the sample notch is in a proximal position with respect to the distal end portion of the cutting cannula, and the drive configured to rotate the toothed rack of the rotatable inner member within the cutting cannula only when the rotatable inner member is in the advanced position.

4. The biopsy device of claim 3, wherein the drive comprises:
   a rotation control gear attached to the toothed rack; and
   a rotation driver gear configured to engage the rotation control gear for rotation of the toothed rack when the rotatable inner member is in the advanced position.

5. The biopsy device of claim 4, comprising an interlock mechanism configured to fix the toothed rack and the cutting cannula relative to each other.

6. The biopsy device of claim 5, wherein the toothed rack and the cutting cannula are rotatable simultaneously only when the rotatable inner member is in the advanced position.

7. The biopsy device of claim 1, the drive configured to rotate the toothed rack in a stepwise movement.

8. The biopsy device of claim 7, wherein the rotation of the toothed rack oscillates between a clockwise direction and a counter-clockwise direction.

9. The biopsy device of claim 8, wherein the rotation angle of the toothed rack relative to the cutting cannula oscillates between −30 and +30 degrees.

10. The biopsy device of claim 1, comprising a cutting mechanism configured to cause the cutting cannula to be longitudinally displaced in a distal direction from a first position at the proximal end of the sample notch wherein the sample notch is exposed, to a second position at the distal end of the sample notch, wherein the cutting mechanism is configured to interchangeably retract and advance the cutting cannula in longitudinal steps during severing of the tissue sample.

11. The biopsy device of claim 10, wherein the size of the longitudinal steps is between 1 and 3 mm.

12. The biopsy device of claim 1, wherein the rotatable inner member is longitudinally movable in the cutting cannula between an advanced position and a retracted position, and the toothed rack is configured such that longitudinal movement of the rotatable inner member to the retracted position can only be provided in a predefined rotational orientation of the toothed rack.

13. The biopsy device of claim 1, the toothed rack having a distal portion that is distal to the proximal portion, the distal portion having second circumferential toothing only located at one side of the toothed rack.

14. The biopsy device of claim 1, the toothed rack having second circumferential toothing that extends in a distal direction beyond the rotation zone of the toothed rack and that is only located at one side of the toothed rack.

15. The biopsy device of claim 1, wherein the cutting cannula has an external shell and at least one longitudinal vacuum channel formed inside the external shell.

16. The biopsy device of claim 1, wherein the cutting cannula has an external shell and a longitudinal vacuum channel that is circumferential inside the external shell.

17. The biopsy device of claim 1, comprising a plurality of the lateral vent holes distributed circumferentially in the cutting cannula.

18. The biopsy device of claim 1, comprising a tissue collection tank configured to collect a tissue sample from the sample notch.

19. The biopsy device of claim 18, wherein the tissue collection tank includes a vacuum port for provision of a vacuum inside the tissue collection tank, and a collection pipe configured to transfer the tissue sample from the sample notch and into the tissue collection tank.

* * * * *